(12) United States Patent
Meerpoel et al.

(10) Patent No.: US 6,583,136 B1
(45) Date of Patent: Jun. 24, 2003

(54) ANTIFUNGAL ETHERS

(75) Inventors: Lieven Meerpoel, Beerse (BE); Leo Jacobus Jozef Backx, Arendonk (BE)

(73) Assignee: Janssen Pharmacuetica N.V., Beerse (BE)

( * ) Notice: Subject to any disclaimer, the term of this patent is extended or adjusted under 35 U.S.C. 154(b) by 0 days.

(21) Appl. No.: 09/980,560

(22) PCT Filed: Apr. 20, 2000

(86) PCT No.: PCT/EP00/03740

§ 371 (c)(1),
(2), (4) Date: Feb. 4, 2002

(87) PCT Pub. No.: WO00/66580

PCT Pub. Date: Nov. 9, 2000

Related U.S. Application Data

(60) Provisional application No. 60/132,699, filed on May 4, 1999.

(51) Int. Cl.$^7$ .................. A61K 31/55; A61K 31/496; C07D 405/14

(52) U.S. Cl. .................. 514/217.05; 514/235.8; 514/252.11; 514/254.07; 544/121; 544/357; 544/366; 544/370; 540/598

(58) Field of Search ............... 544/366, 370, 544/121, 357; 514/254.07, 217.05, 235.8, 252.11; 540/598

(56) References Cited

U.S. PATENT DOCUMENTS

| | | | |
|---|---|---|---|
| 3,459,731 A | 8/1969 | Gramera et al. | 260/209 |
| 4,267,179 A | 5/1981 | Heeres et al. | 424/25 D |
| 4,619,931 A | 10/1986 | Heeres et al. | 514/252 |
| 4,791,111 A | 12/1988 | Heeres et al. | 514/252 |
| 4,931,444 A | 6/1990 | Van Wauwe et al. | 514/252 |
| 5,006,513 A | 4/1991 | Hector et al. | 514/43 |

FOREIGN PATENT DOCUMENTS

| | | |
|---|---|---|
| EP | 0 118 138 | 9/1984 |
| EP | 0 228 125 | 7/1987 |
| WO | WO 95/17407 | 7/1987 |
| WO | WO 96/38443 | 6/1995 |
| WO | WO 97/00255 | 1/1997 |
| WO | WO 97/18839 | 5/1997 |
| WO | WO 98/34934 | 8/1998 |

OTHER PUBLICATIONS

Mertin, D., et al., "In–vitro permeability of the human nail and of a keratin membrane from bovine hooves: influence of the partition coefficient octanol/water and the water solubility of drugs on their permeability and maximum flux," *J. Pharm.* 1997, 49, 30–34.

Nogradi, M., "Dimethyl–β–cyclodextrin," *Drugs in the Future*, 1984, 9(8), 577–578.

Odds, F.C., "Quantitative microculture system with standardized inocula for strain typing, susceptibility testing, and other physiologic measurements with Canadia albicans and other yeasts," *J. Clinical Microbiology*, Dec. 1991, 29(12), 2735–2740.

*Primary Examiner*—Emily Bernhardt
(74) *Attorney, Agent, or Firm*—Woodcock Washburn LLP

(57) ABSTRACT

The present invention concerns compounds of formula (I)

the N-oxide forms, the salts, the quaternary amines and stereochemically isomeric forms thereof, wherein D represents a tetrahydrofuran or dioxolane ring substituted with aryl and azolmethyl; —A—B— represents an optionally substituted bivalent radical of formula —N=CH—, —CH=N—, —CH=CH—, —CH$_2$—CH$_2$; Alk represents C$_{1-6}$alkanediyl; Y represents optionally substituted C$_{1-6}$alkanediyl; R$^1$ and R$^2$ represent hydrogen, C$_{1-6}$alkyl or arylC$_{1-6}$alkyl; or R$^1$ and R$^2$ may be taken together to form an optionally substituted heterocyclic radical selected from morpholinyl, pyrrolidinyl, piperidinyl, homopiperidinyl, piperazinyl or phthalimid-1-yl; aryl represents phenyl, naphthalenyl, 1,2,3,4-tetrahydro-naphthalenyl, indenyl or indanyl; each of said aryl groups may optionally be substituted; having broad-spectrum antifungal activity; their preparation, compositions containing them and their use as a medicine.

10 Claims, No Drawings

ANTIFUNGAL ETHERS

This application is a National Stage application under 35 U.S.C. §371 of PCT/EP00/03740 filed Apr. 20, 2000, which claims priority from provisional application 60/132,699, filed May 4, 1999.

The present invention is concerned with water soluble azole containing ethers as broad-spectrum antifungals and their preparation; it further relates to compositions comprising them, as well as their use as a medicine.

Systemic fungal infections in man are relatively rare in temperate countries and many of the fungi that can become pathogenic normally live commensally in the body or are common in the environment. The past few decades have witnessed an increasing incidence of numerous life-threatening systemic fungal infections world-wide and these now represent a major threat to many susceptible patients, particularly those already hospitalized. Most of the increase can be attributed to improved survival of immuno-compromised patients and the chronic use of antimicrobial agents. Moreover, the flora typical of many common fungal infections is also changing and this is presenting an epidemiological challenge of increasing importance. Patients at greatest risk include those with impaired immune functioning, either directly as a result of immunosuppression from cytotoxic drugs or HIV infection, or secondary to other debilitating diseases such as cancer, acute leukaemia, invasive surgical techniques or prolonged exposure to antimicrobial agents. The most common systemic fungal infections in man are candidosis, aspergillosis, histoplasmosis, coccidioidomycosis, paracoccidioidomycosis, blastomycosis and cryptococcosis.

Antifungals such as ketoconazole, itraconazole and fluconazole are employed for the treatment and prophylaxis of systemic fungal infections in immuno-compromised patients. However, concern is growing about fungal resistance to some of these agents, especially these with a relatively narrow spectrum, e.g. fluconazole. Worse still, it is recognized in the medical world that about 40% of the people suffering from severe systemic fungal infections are hardly, or not at all, able to receive medication via oral administration. This inability is due to the fact that such patients are in coma or suffer from severe gastroparesis. Hence, the use of insoluble or sparingly soluble antifungals such as itraconazole, that are difficult to administer intravenously, is heavily impeded in this group of patients.

Also the treatment of onychomycosis, i.e. fungal infection of the nails, may well be served by potent water soluble antifungals. It is long desired to treat onychomycosis via the transungual route. The problem that then arises is to ensure that the antifungal agents will penetrate into and beneath the nail. Mertin and Lippold (J. Pharm.

Pharmacol. (1997), 49, 30–34) stated that in order to screen for drugs for topical application to the nail plate, attention has to be paid mainly to the water solubility of the compound. The maximum flux through the nail is beneficially influenced by increasing the water solubility of the antifungal. Of course, efficacy in treating onychomycosis via the transungual route is also dependent on the potency of the antifungal.

Consequently, there is a need for new antifungals, preferably broad-spectrum antifungals, against which there is no existing resistance and which can be administered intravenously or transungually. Preferably the antifungal should also be available in a pharmaceutical composition suitable for oral administration. This enables the physician to continue treatment with the same drug after the patient has recovered from the condition which required intravenous or transungual administration of said drug.

U.S. Pat. No. 4,267,179 discloses heterocyclic derivatives of (4-phenylpiperazin-1-yl-aryloxy-methyl-1,3-dioxolan-2-yl)-methyl-1H-imidazoles and 1H-1,2,4-triazoles useful as antifungal agents. Said patent encompasses itraconazole, which is available as a broad-spectrum antifungal on a world-wide basis.

EP-A-0, 118,138 and EP-A-0,228,125 disclose 4-[4-[4-[4-[[2-aryl-2-azolyl-1,3dioxolan-4-yl]methoxy]phenyl]-1-piperazinyl]phenyl]-2,4-dihydro-2-alkyloxyalkyl-3H-1,2,4-triazol-3-one derivatives as antifungals. WO 95/17407 discloses tetrahydrofuran antifungals as well as WO 96/38443 and WO 97/00255. The latter two publications disclose tetrahydrofuran antifungals, which are taught to be soluble and/or suspendible in an aqueous medium suitable for intravenous administration, containing substitution groups readily convertible in vivo into hydroxy groups.

Unexpectedly, the compounds of the present invention are potent broad-spectrum antifungals with good water solubility.

The present invention concerns compounds of formula

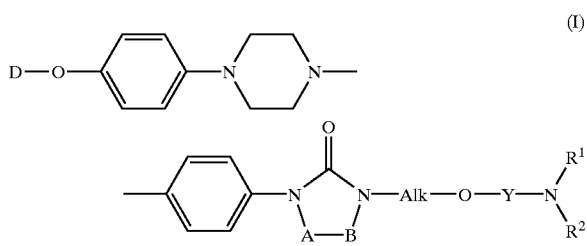

the N-oxide forms, the salts, the quaternary amines and stereochemically isomeric forms thereof, wherein D represents a radical of formula

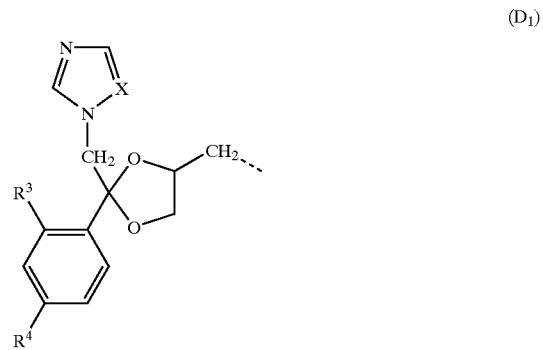

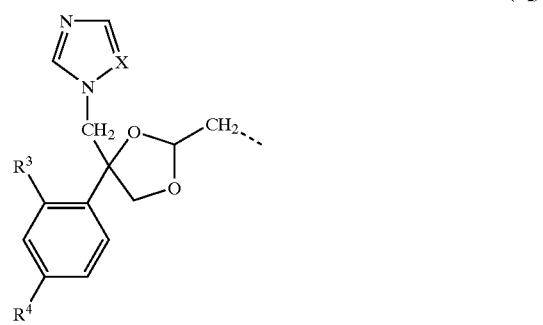

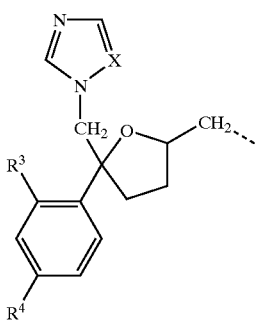
(D₃)

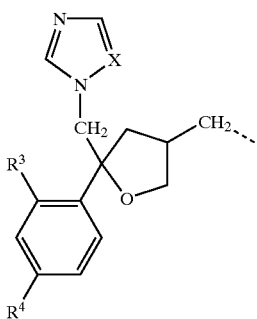
(D₄)

wherein the dotted line represents the bond attaching D to the remainder of the compound of formula (1);
X is N or CH;
R³ is hydrogen or halo;
R⁴ is halo;
—A—B— represents a bivalent radical of formula —N=CH— (i),
—CH=N— (ii),
—CH=CH— (iii),
—CH₂—CH₂ (iv), wherein one hydrogen atom in the radicals (i) and (ii) may be replaced by a $C_{1-4}$alkyl radical and one or more hydrogen atoms in radicals (iii) and (iv) may be replaced by a $C_{1-4}$alkyl radical;
Alk represents $C_{1-6}$alkanediyl;
Y represents $C_{1-6}$alkanediyl optionally substituted with one or two substituents selected from halo, hydroxy, mercapto, $C_{1-4}$alkyloxy, $C_{1-4}$alkylthio, aryloxy, arylthio, aryl$C_{1-4}$alkyloxy, aryl$C_{1-4}$alkylthio, cyano, amino, mono- or di($C_{1-4}$alkyl)amino, mono- or di(aryl)amino, mono- or di(aryl$C_{1-4}$alkyl)amino, $C_{1-4}$alkyloxycarbonylamino, benzyloxycarbonylamino, aminocarbonyl, carboxyl, $C_{1-4}$alkyloxycarbonyl, guanidinyl, aryl and Het;
R¹ represents hydrogen, $C_{1-4}$alkyl or aryl$C_{1-6}$alkyl; R² represents hydrogen, $C_{1-4}$alkyl or aryl$C_{1-6}$alkyl; or R¹ and R² may be taken together to form a heterocyclic radical selected from morpholinyl, pyrrolidinyl, piperidinyl, homopiperidinyl, piperazinyl or phthalimid-1-yl; said heterocyclic radical may optionally be substituted with $C_{1-4}$alkyl, aryl, Het, aryl$C_{1-4}$alkyl, Het$C_{1-4}$alkyl, hydroxy$C_{1-4}$alkyl, amino, mono- or di($C_{1-4}$alkyl)amino, amino$C_{1-4}$alkyl, mono- or di($C_{1-4}$alkyl)amino$C_{1-4}$alkyl, carboxyl, aminocarbonyl, $C_{1-4}$alkyloxycarbonyl; $C_{1-4}$alkyloxycarbonylamino or mono- or di($C_{1-4}$alkyl)aminocarbonyl;

aryl represents phenyl, naphthalenyl, 1,2,3,4-tetrahydro-naphthalenyl, indenyl or indanyl; each of said aryl groups may optionally be substituted with one or more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy$C_{1-4}$alkyl, amino$C_{1-4}$alkyl, mono- or di($C_{1-4}$alkyl)amino$C_{1-4}$alkyl;

Het represents a monocyclic or bicyclic heterocyclic radical; said monocyclic heterocyclic radical being selected from the group piperazinyl, homopiperazinyl, 1,4-dioxanyl, morpholinyl, thiomorpholinyl, pyridyl, piperidinyl, homopiperidinyl, pyrazinyl, pyrimidinyl, pyridazinyl, triazinyl, triazolyl, pyranyl, tetrahydropyranyl, imidazolyl, imidazolinyl, imidazolidinyl, pyrazolyl, pyrazolinyl, pyrazolidinyl, thiazolyl, thiazolidinyl, isothiazolyl, oxazolyl, oxazolidinyl, isoxazolyl, pyrrolyl, pyrrolinyl, pyrrolidinyl, furanyl, tetrahydrofuranyl, thienyl, thiolanyl, dioxolanyl; said bicyclic heterocyclic radical being selected from the group quinolinyl, 1,2,3,4-tetrahydroquinolinyl, isoquinolinyl, quinoxalinyl, quinazolinyl, phtalazinyl, cinnolinyl, chromanyl, thiochromanyl, 2H-chromenyl, 1,4-benzodioxanyl, indolyl, isoindolyl, indolinyl, indazolyl, purinyl, pyrrolopyridinyl, furanopyridinyl, thienopyridinyl, benzothiazolyl, benzoxazolyl, benzisothiazolyl, benzisoxazolyl, benzimidazolyl, benzofuranyl, benzothienyl; whereby each of said mono- or bicyclic heterocycle may optionally be substituted with one or where possible more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy-$C_{1-4}$alkyl, amino$C_{1-4}$alkyl, mono- or di($C_{1-4}$alkyl)amino$C_{1-4}$alkyl, aryl or aryl$C_{1-4}$alkyl.

As used in the foregoing definitions and hereinafter halo defines fluoro, chloro, bromo and iodo; $C_{1-4}$alkyl as a group or part of a group encompasses the straight and branched chain saturated hydrocarbon radicals having from 1 to 4 carbon atoms such as, for example, methyl, ethyl, propyl, butyl and the like; $C_{1-6}$alkyl as a group or part of a group encompasses the straight and branched chain saturated hydrocarbon radicals as defined in $C_{1-4}$alkyl as well as the higher homologues thereof containing 5 or 6 carbon atoms such as, for example, pentyl or hexyl; $C_{1-6}$alkanediyl encompasses the straight and branched chain saturated bivalent hydrocarbon radicals having from 1 to 6 carbon atoms such as, for example, methylene, 1,2-ethanediyl, 1,3-propanediyl, 1,4-butanediyl, 1,5-pentanediyl, 1,6-hexanediyl, 1,2-propanediyl, 1,2-butanediyl, 2,3-butanediyl and the like; $C_{2-3}$alkanediyl encompasses the straight and branched chain saturated bivalent hydrocarbon radicals having 2 or 3 carbon atoms such as, for example, 1,2-ethanediyl, 1,2-propanediyl and 1,3-propanediyl.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form. The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be made using ion exchange resin columns.

The term "stereochemically isomeric forms" as used hereinbefore defines all the possible stereoisomeric forms in which the compounds of formula (I) exist, thus, also including all enantiomers, enantiomeric mixtures and diastereomeric mixtures. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' being equivalent to 'chirally pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

The terms cis and trans are used herein in accordance with Chemical Abstracts nomenclature and refer to the position of the substituents on a ring moiety, more in particular on the tetrahydrofuran ring or the dioxolane ring in the compounds of formula (I). For instance, when establishing the cis or trains configuration of a tetrahydrofuran or dioxolane ring in a radical of formula $(D_1)$, $(D_2)$, $(D_3)$ or $(D_4)$, the substituent with the highest priority on the carbon atom in the 2 position of the tetrahydrofuran or dioxolane ring, and the substituent with the highest priority on the carbon atom in the 4 position of the tetrahydrofuran or dioxolane ring in the radicals of formula $(D_1)$, (D2) or $(D_4)$ or the 5 position of the tetrahydrofuran ring in the radical of formula $(D_3)$ are considered (the priority of a substituent being determined according to the Cahn-Ingold-Prelog sequence rules). When said two substituents with highest priority are at the same side of the ring then the configuration is designated cis, if not, the configuration is designated trans.

The compounds of formula (I) all contain at least 2 asymmetric centers which may have the R- or S-configuration. As used herein, the stereochemical descriptors denoting the stereochemical configuration of each of the 2 or more asymmetric centers are also in accordance with Chemical Abstracts nomenclature.

Of some compounds of formula (I) and of intermediates used in their preparation, the absolute stereochemical configuration was not experimentally determined. In those cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

The N-oxide forms of the present compounds are meant to comprise the compounds of formula (I) wherein one or several nitrogen atoms are oxidized to the so-called N-oxide.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest arc those compounds of formula (I) which are stereochemically pure.

An interesting group of compounds are those compounds of formula (I) wherein —Alk— is a bivalent radical of formula

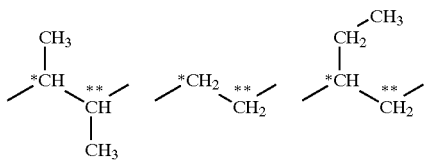

wherein the carbon atom marked with one asterisk is attached to the nitrogen atom and the carbon atom marked with two asterisks is attached to the oxygen atom.

Also interesting are those compounds of formula (I) wherein D is a radical of formula $D_1$ or $D_2$, in particular $D_1$. Suitably, $R^3$ and $R^4$ are both a halogen, more in particular a chloro or fluoro atom, and X is a nitrogen atom.

Further —A—B— suitably is a radical of formula (ii).

A particular group of compounds are those compounds of formula (I) wherein Y is $C_{1-6}$alkanediyl optionally substituted with aryl; more in particular, $C_{2-3}$alkanediyl optionally substituted with aryl.

A preferred group of compounds are those compounds of formula (1) wherein D is a radical of formula $D_1$, X is a nitrogen atom, $R^3$ and $R^4$ are both a halogen, —Alk— is a bivalent radical of formula

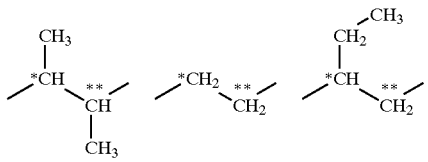

wherein the carbon atom marked with an asterisk is attached to the nitrogen atom and the carbon atom marked with two asterisks is attached to the oxygen atom and Y is $C_{2-3}$alkanediyl optionally substituted with aryl.

The compounds of the present invention can be prepared by reacting an intermediate of formula (II) wherein $W^1$ is a suitable leaving group such as, for example, a halogen, e.g. iodo, an arylsulfonyloxy or an alkanesulfonyloxy group, e.g. p-toluenesulfonyloxy, naphthylsulfonyloxy or methanesulfonyloxy, with an intermediate of formula (III) in a reaction-inert solvent such as, for example, N,N-dimethylformamide, N,N-dimethylacetamide, 1-methyl-2-pyrrolidinone, 1,3-dimethyl-2-imidazolidinone, sulfolane or the like, and in the presence of a suitable base such as, for example, sodium hydroxide or sodium hydride.

(amylose 3,5 dimethylphenyl carbamate) or Chiralpak AS, both purchased from Daicel Chemical Industries, Ltd, in Japan.

Compounds of formula (I) may also be prepared by N-alkylating an intermediate of formula (IV) with an intermediate of formula (V) wherein $W^2$ is a suitable leaving group such as, for example, a halogen, and in case $R^1$ and/or R is hydrogen, the primary or secondary amine group is protected with a protective group P such as, for example, a $C_{1-4}$alkyloxycarbonyl group or a benzyl group, in a reaction-inert solvent such as, for example, dimethylsulfoxide, in the presence of a base such as, for example, potassium hydroxide. In case the amine was protected, art-known deprotection techniques can be employed to arrive at compounds of formula (I) after the N-alkylation reaction.

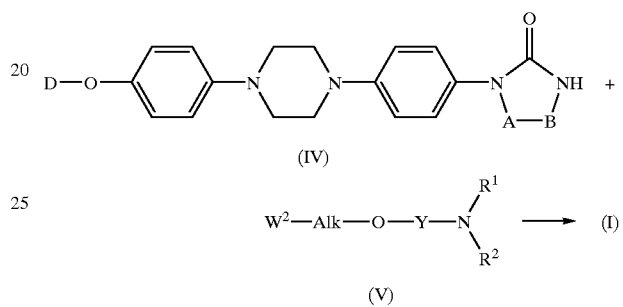

Compounds of formula (I) may also be prepared by reacting an intermediate of formula (VI) with an intermediate of formula (VII) wherein W3 is a suitable leaving group such as, for example, a halogen, an arylsulfonyloxy or an alkanesulfonyloxy group, e.g. p-toluenesulfonyloxy, naphthylsulfonyloxy or methanesulfonyloxy, optionally in the presence of a suitable base such as, for example, sodium hydride, and optionally in a reaction-inert solvent such as, for example, N,N-dimethylformamide, N,N-dimethylacetamide, toluene, 1-methyl-2-pyrrolidinone, 1,3-dimethyl-2-imidazolidinone, sulfolane or the like. In case $R^1$ and/or $R^2$ is hydrogen, the primary or secondary amine group may be protected with a protective group P such as, for example, a $C_{1-4}$alkyloxycarbonyl group or a benzyl group, and after the O-alkylation reaction, art-known deprotection techniques can be employed to arrive at compounds of formula (I)

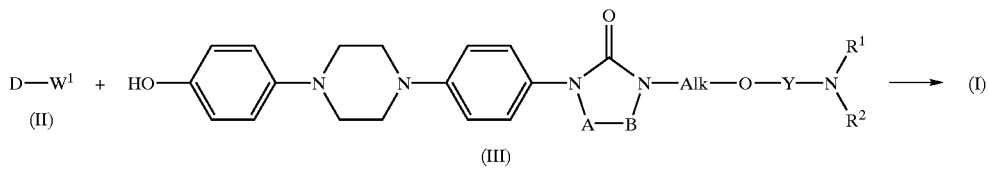

In this and the following preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak AD

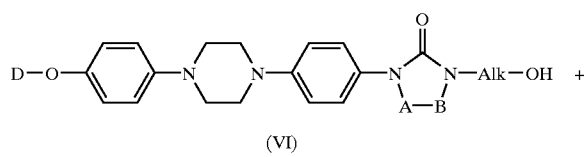

-continued

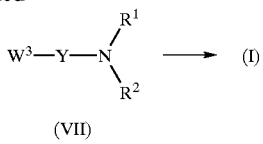

(VII)

The compounds of formula (I) may also be converted into each other following art-known transformations.

Compounds of formula (I) containing a $C_{1-4}$alkyloxycarbonylamino moiety may be converted to compounds of formula (I) containing the corresponding amino moiety using art-known techniques such as, for example, reaction in dichloromethane and in the presence of trifluoroacetic acid.

Compounds of formula (I) containing a primary amine may be mono-methylated by first protecting the primary amine with a suitable protecting group such as, for example, an arylalkyl group, e.g. benzyl; and subsequently methylating the secondary amine using art-known methylation techniques such as, for example, reaction with paraformaldehyde. The thus obtained tertiary amine may be deprotected using art-known deprotection techniques such as, for example, reaction with hydrogen in tetrahydrofuran or methanol and in the presence of a catalyst such as, for example palladium-on-charcoal, thus obtaining the desired methylated secondary amine.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the intermediates and starting materials used in the above reaction procedures are commercially available, or may be synthesized according to procedures described elsewhere, e.g. U.S. Pat. No. 4,619,931, U.S. Pat. No. 4,791,111, U.S. Pat. No. 4,931,444, U.S. Pat. No. 4,267,179 and WO 98/34934.

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases.

Enantiomers may be separated from each other by the selective crystallization of their diastereomeric salts with optically active acids. Alternatively, enantiomers may be separated by chromato-graphic techniques using chiral stationary phases. Said pure stereoisomeric forms may also be derived from the corresponding pure stereoisomeric forms of the appropriate starting materials, provided that the reaction occurs stereo-selectively or stereospecifically. Preferably if a specific stereoisomer is desired, said compound will be synthesized by stereoselective or stereospecific methods of preparation. These methods will advantageously employ chirally pure starting materials. Stereoisomeric forms of the compounds of formula (1) are obviously intended to be included within the scope of the invention.

The chirally pure forms of the compounds of formula (I) form a preferred group of compounds. It is therefore that the chirally pure forms of the intermediates of formula (II), (III) and (VI), their N-oxide forms, their salt forms and their quaternary amines are particularly useful in the preparation of chirally pure compounds of formula (I). Also enantiomenc mixtures and diastereomeric mixtures of intermediates of formula (II), (III) and (VI) are useful in the preparation of compounds of formula (I) with the corresponding configuration.

The compounds of formula (I), the salts, the quaternary amines and the stereochemically isomeric forms thereof are useful agents for combating fungi in vivo. The present compounds are broad-spectrum antifungals. They are active against a wide variety of fungi, such as Candida spp., e.g. *Candida albicans, Candida glabrata, Candida krusei, Candida parapsilosis, Candida kefyr, Candida tropicalis*; Aspergillus spp., e.g. *Aspergillus fumigatus, Aspergillus niger, Aspergillus flavus; Cryptococcus neoformans; Sporothrix schenckii*; Fonsecaea spp.; *Epidermophyton floccosum; Microsporum canis*; Trichophyton spp.; Fusarium spp.; and several dematiaceous hyphomycetes. Of particular interest is the improved activity of some of the present compounds against Fusarium spp.

In vitro experiments, including the determination of the fungal susceptibility of the present compounds as described in the pharmacological example hereinafter, indicate that the compounds of formula (I) have a favourable intrinsic inhibitory capacity on fungal growth in for instance *Candida albicans*. Other in vitro experiments such as the determination of the effects of the present compounds on the sterol synthesis in, for instance, *Candida albicans*, also demonstrate their antifungal potency. Also in vivo experiments in several mouse, guinea-pig and rat models show that, after both oral and intravenous administration, the present compounds are potent antifungals.

An additional advantage of some of the present compounds is that they are not only fungistatic, as most of the known azole antifungals, but are also fungicidal at acceptable therapeutic doses against many fungal isolates.

The compounds of the present invention are chemically stable and have a good oral availability.

The solubility profile in aqueous solutions of the compounds of formula (I) makes them suitable for intravenous administration. Particularly interesting compounds are those compounds of formula (I) having a water-solubility of at least 0.1 mg/ml at a pH of at least 4, preferably, a water-solubility of at least 1 mg/ml at a pH of at least 4, and more preferred a water-solubility of at least 5 mg/ml at a pH of at least 4.

In view of the utility of the compounds of formula (I), there is provided a method of treating warm-blooded animals, including humans, suffering from fungal infections. Said method comprises the systemic or topical administration of an effective amount of a compound of formula (I), a N-oxide form, a salt, a quaternary amine or a possible stereoisomeric form thereof, to warm-blooded animals, including humans. Hence, compounds of formula (I) are provided for use as a medicine, in particular, the use of a compound of formula (I) in the manufacture of a medicament useful in treating fungal infections is provided.

The present invention also provides compositions for treating or preventing fungal infections comprising a therapeutically effective amount of a compound of formula (I) and a pharmaceutically acceptable carrier or diluent.

In view of their useful pharmacological properties, the subject compounds may be formulated into various pharmaceutical forms for administration purposes. To prepare the pharmaceutical compositions of this invention, a therapeutically effective amount of a particular compound, in base or addition salt form, as the active ingredient is combined in intimate admixture with a pharmaceutically acceptable carrier, which.carrier may take a wide variety of forms depending on the form of preparation desired for administration. These pharmaceutical compositions are desirably in unitary dosage form suitable, preferably, for administration orally, rectally, topically, percutaneously, transungually or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, emulsions, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. As appropriate compositions for topical application there may be cited all compositions usually employed for topically administering drugs e.g. creams, gel, dressings, shampoos, tinctures, pastes, ointments, salves, powders and the like. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

Transungual compositions are in the form of a solution and the carrier optionally comprises a penetration enhancing agent which favours the penetration of the antifungal into and through the keratinized ungual layer of the nail. The solvent medium comprises water mixed with a co-solvent such as an alcohol having from 2 to 6 carbon atoms, e.g. ethanol.

For parenteral compositions, the carrier will usually comprise sterile water, at least in large part. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. For parenteral compositions, also other ingredients, to aid solubility for example, e.g. cyclodextrins, may be included. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$ alkyl, particularly carboxymethyl or carboxyethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:

a) dissolving the compound of formula (I) and the water-soluble polymer in an appropriate solvent, optionally at elevated temperatures;

b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:

a) mixing a compound of formula (I) and an appropriate water-soluble polymer, b) optionally blending additives with the thus obtained mixture, c) heating and compounding the thus obtained blend until one obtains a homogenous melt, d) forcing the thus obtained melt through one or more nozzles; and e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product can be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa.s more preferably of 1 to 700 mPa.s, and most preferred of 1 to 100 mPa.s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinyl-pyrrolidone with vinyl acetate, combinations of polyvinylalcohol and polyvinyl-pyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxy-ethyl.

As used hereinbefore, $C_{1-2}$alkyl represents straight or branched chain saturated hydrocarbon radicals having 1 or 2 carbon atoms such as methyl or ethyl; $C_{1-3}$alkyl encompasses the straight and branched chain saturated hydrocarbon radicals as defined in $C_{1-2}$alkyl as well as the higher homologue thereof containing 3 carbon atoms, such as propyl; $C_{2-4}$alkyl represents straight or branched chain saturated hydrocarbon radicals having from 2 to 4 carbon atoms such as ethyl, propyl, butyl, 1-methyl-propyl and the like.

Of particular utility are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another suitable type of substituted cyclodextrins is sulfobutylcyclodextrines.

The ratio of active ingredient over cyclodextrin may vary widely. For example ratios of 1/100 to 100/1 may be applied. Interesting ratios of active ingredient over cyclodextrin range from about 1/10 to 10/1. More interesting ratios of active ingredient over cyclodextrin range from about 1/5 to 5/1.

It may further be convenient to formulate the present azole antifungals in the form of nanoparticles which have a surface modifier adsorbed on the surface thereof in an amount sufficient to maintain an effective average particle size of less than 1000 nm. Useful surface modifiers are believed to include those which physically adhere to the surface of the antifungal agent but do not chemically bond to the antifungal agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present antifungals are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and an antifungal agent and a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The pharmaceutical compositions mentioned above may also contain a fungicidally effective amount of other antifungal compounds such as cell wall active compounds. The term "cell wall active compound", as used herein, means any compound which interferes with the fungal cell wall. Appropriate antifungal compounds for use in combination with the present compounds include, but are not limited to, known azoles such as fluconazole, voriconazole, itraconazole, ketoconazole, miconazole, ER 30346, SCH 56592; polyenes such as amphotericin B, nystatin or liposomal and lipid forms thereof, such as Abelcet, AmBisome and Amphocil; purine or pyrimidine nucleotide inhibitors such as flucytosine; polyoxins and nikkcomycins, in particular nikkomycin Z or nikkomycin K and others which are described in U.S. Pat. No. -5,006,513 or other chitin inhibitors; elongation factor inhibitors such as sordarin and analogs thereof; mannan inhibitors such as predamycin; bactericidal/permeability-inducing (BPI) protein products such as XMP.97 or XMP.127; complex carbohydrate antifungal agents such as CAN-296; (1,3)-β-glucan synthase inhibitors including papulacandins, aculeacins, and echinocandins.

It is especially advantageous to formulate the aforementioned pharmaceutical compositions in unit dosage form for ease of administration and uniformity of dosage. Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, teaspoonfuls, tablespoonfuls and the like, and segregated multiples thereof.

Those of skill in treating warm-blooded animals suffering from diseases caused by fungi could easily determine the therapeutically effective daily amount from the test results given herein. In general, it is contemplated that a therapeutically effective daily amount would be from 0.05 mg/kg to 20 mg/kg body weight.

EXPERIMENTAL PART

Hereinafter, "DMF" is defined as N,N-dimethylformamide and "DIPE" is defined as diisopropylether.

A. PREPARATION OF THE INTERMEDIATES

Example A1 a) A mixture of 2,4-dihydro4-[4-[4-(4-methoxyphenyl)-1-piperazinyl]phenyl]-3H-1,2,4-triazol-3-one (0.05 mol), 2-bromo-butanoic acid ethyl ester (0.055 mol) and $Na_2CO_3$ (0.15 mol) in 1-methyl-2-pyrrolidinone (250 ml) was stirred at 75° C. over 2-Bromobutanoic acid ethyl ester (0.015 mol) was added again. The mixture was stirred at 75° C. for 6 hours, at room temperature for 48 hours, poured out into $H_2O$ and stirred for 30 minutes. The precipitate was filtered off and dissolved in $CH_2Cl_2$. The solution was filtered. The filtrate was dried, filtered and the solvent was evaporated. The residue was triturated in diisopropylether and ethylacetate, filtered off and dried, yielding 10 g (43%) of (±)-ethyl α-ethyl-4,5-dihydro-4-[4-[4-(4-methoxyphenyl)-1-piperazinyl ]phenyl]-5-oxo- 1H-1,2,4-triazol-1-acetate (interm. 1).

b) A mixture of $NaHSO_3$ (1 g) in HBr 48% (250 ml) and a acetic acid/HBr mixture (250 ml) was stirred for 15 minutes. Intermediate 1 (0.022 mol) was added. The mixture was stirred and refluxed for 90 minutes. The solvent was evaporated. Toluene was added and evaporated. The residue was dissolved in $CH_3OH$. The mixture was stirred on an ice bath. $SOCl_2$ (24 g) was added dropwise. The mixture was stirred overnight. The solvent was evaporated. The residue was dissolved in $CH_2Cl_2$. The organic solution was washed with a $NaHCO_3$ solution, dried, filtered and the solvent was evaporated. The residue was triturated in DIPE, filtered off and dried, yielding 6.6 g (±)-methyl α-ethyl4,5-dihydro4-[4-[4-(4-hydroxyphenyl)-1-piperazinyl]phenyl]-5-oxo-1H-1,2,4-triazol-1-acetate (interm. 2).

c) A mixture of (−)-(2S-cis)-2-(2,4-difluorophenyl)-2-(1H-1,2,4-triazol-1-ylmethyl)-1,3-dioxolane-4-methanol methanesulfonate(ester) (0.007 mol), intermediate (2) (0.0068 mol) and NaOH (0.008 mol) in DMF (100 ml) was stirred at 50° C. under $N_2$ flow overnight, then poured out into $H_2O$ and stirred for 1 hour. The precipitate was filtered off and dissolved in $CH_2Cl_2$. The organic layer was separated, dried, filtered and the solvent was evaporated. The residue was purified by column chromatography over silica gel (eluent: $CH_2Cl_2/CH_3OH$/hexane/ethyl acetate 48/2/20/30). The pure fractions were collected and the solvent was evaporated. The residue was triturated in ethyl acetate, filtered off and dried, yielding 1.4 g (29%) of methyl (2S-cis)-4-[4-[4-[[2-(2,4-difluorophenyl)-2-(1H-1,2,4-triazol-1-ylmethyl )-1,3-dioxolan-4-yl]methoxy]-phenyl]-1-piperazinyl]phenyl]-α-ethyl4,5-dihydro-5-oxo-1H-1,2,4-triazol-1-acetate (interm. 3a).

In an analogous way, intermediate 3b was prepared.

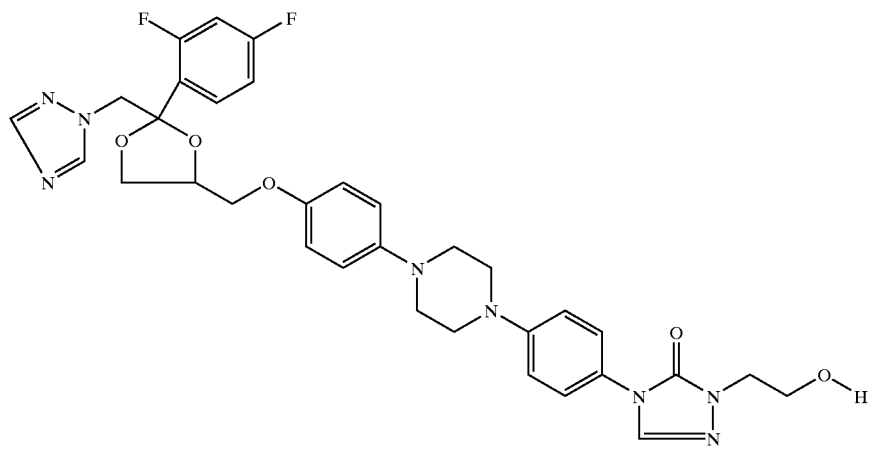

intermediate 3b (2S-cis)

d) A mixture of intermediate (3a) (0.009 mol) and NaBH$_4$ (0.045 mol) in dioxane (300 ml) and H$_2$O (100 ml) was stirred at room temperature overnight. A saturated NH$_4$Cl solution (100 ml) was added. The mixture was stirred for 3 hours. HCl (10 ml) was added. The mixture was stirred for 48 hours, then neutralized with a Na$_2$CO$_3$ solution and extracted with CH$_2$Cl$_2$. The organic layer was separated, washed, dried, filtered and the solvent was evaporated. The residue was purified by column chromatography over silica gel (eluent: CH$_2$Cl$_2$/CH$_3$OH 96/4). The pure fractions were collected and the solvent was evaporated. The residue was triturated in DIPE, filtered off and dried, yielding 4.2 g (68%) (2S-cis)4-[4-[4-[4[[2-(2,4-difluorophenyl)-2-(1H-1, 2,4-triazol-1-ylmethyl)-1,3-dioxolan4-yl]methoxy]phenyl]-1-piperazinyl]phenyl]-2,4-dihydro-2-[1-(hydroxymethyl) propyl]-3H-1,2,4-triazol-3-one (interm. 4).

B. PREPARATION OF THE FINAL COMPOUNDS

Example B1

Preparation of Compound 5

A mixture of intermediate 4 (0.006 mol) and 2-chloro-N, N-diethyl-ethanamine hydrochloride (0.009 mol) in DMF (100 ml) was stirred at 50° C. under N$_2$ flow. NaH (0.018 mol) was added. The mixture was stirred at 50° C. under N$_2$ flow overnight, then poured out into H$_2$O and stirred for 30 minutes. The precipitate was filtered off and dissolved in CH$_2$Cl$_2$. The organic solution was washed, dried, filtered and the solvent was evaporated. The residue was purified by column chromatography over silica gel (eluent: CH$_2$Cl$_2$/(CH$_3$OH/NH$_3$) 98/2). The pure fractions were collected and the solvent was evaporated. The residue was triturated in DIPE, filtered off and dried. The residue was purified by HPLC over silica gel (eluent: CH$_2$Cl$_2$/CH$_3$OH/(CH$_3$OH/NH$_3$) 96/2/2). The pure fractions were collected and the solvent was evaporated. The residue was triturated in DIPE, filtered off and dried, yielding 0.95 g of compound 5.

Example B2

Preparation of Compound 3

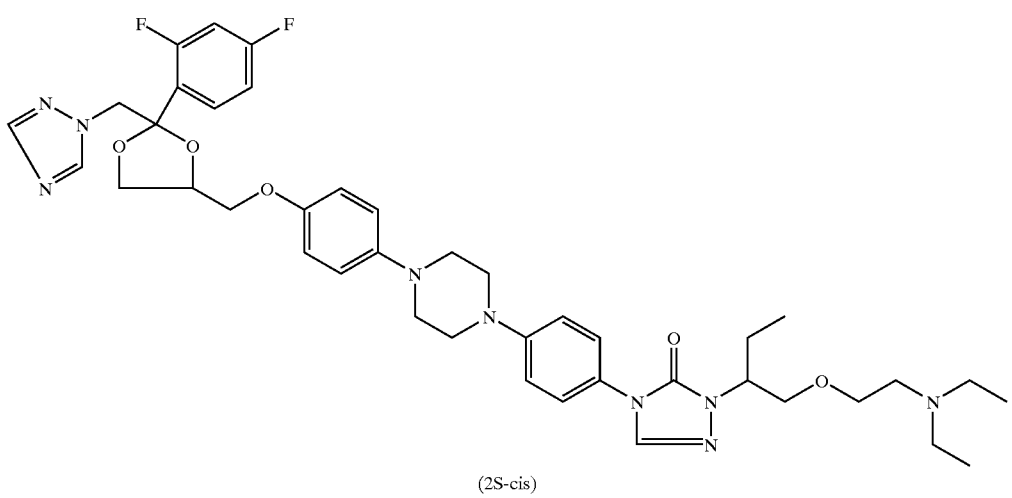

compound 5

(2S-cis)

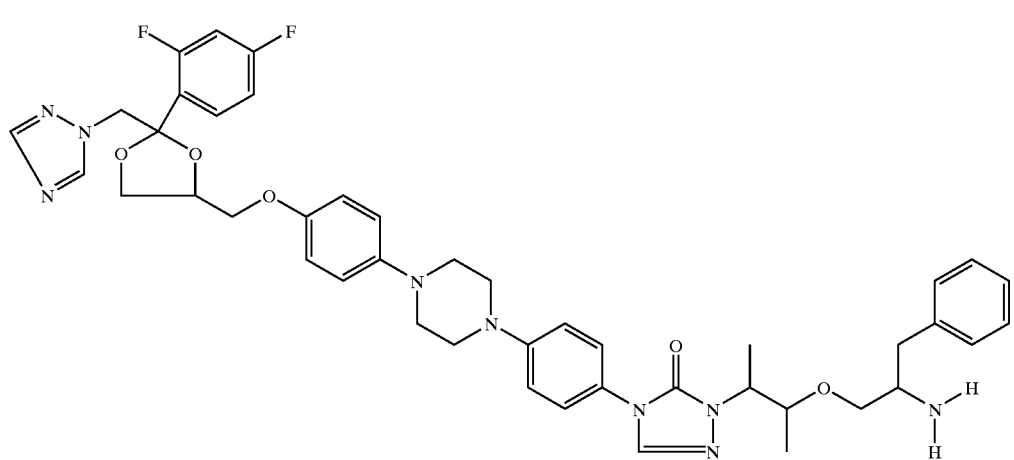

compound 3

[2S-[2α,4α[(R*,R*)(R*)]]]

A mixture of compound 2 (see Table 1) (0.0062 mol), prepared according to the procedure described in example B1, in tetrahydrofuran (150ml) was hydrogenated for 6 days with palladium-on-charcoal 10% (2 g) as a catalyst. After uptake of hydrogen (2 equiv), the catalyst was filtered off and the filtrate was evaporated. The residue was purified over silica gel on a glass filter (eluent: $CH_2Cl_2/CH_3OH$ 98/2 and 97/3). The pure fractions were collected and the solvent was evaporated. The residue was crystallized from 2-propanol. The precipitate was filtered off and dried, yielding 1.37 g (27%) of compound 3.

Table 1 lists the compounds which were prepared analogous to example B1 or B2.

TABLE 1

| Comp. No. | Ex. No. | L | stereochemistry; optical rotation and/or melting point |
|---|---|---|---|
| 1 | B1 | | [2S-[2α,4α(R*,R*)]]; $[α]_{20}^D$ = −24.42 at concentration of 24.98 mg/5 ml methanol |
| 2 | B1 | | [2S-[2α,4α[(R*,R*)(R*)]]] |
| 3 | B2 | | [2S-[2α,4α[(R*,R*)(R*)]]]; $[α]_{20}^D$ = −30.76 at concentration of 25.03 mg/5 ml DMF; mp. 128.7° C. |
| 4 | B1 | | 2S-cis; $[α]_{20}^D$ = −12.15 at concentration of 25.11 mg/5 ml DMF |
| 5 | B1 | | 2S-cis |

TABLE 1-continued

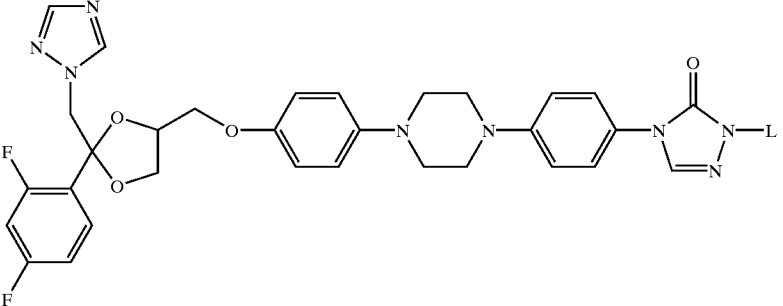

| Comp. No. | Ex. No. | L | stereochemistry; optical rotation and/or melting point |
|---|---|---|---|
| 6 | B1 | 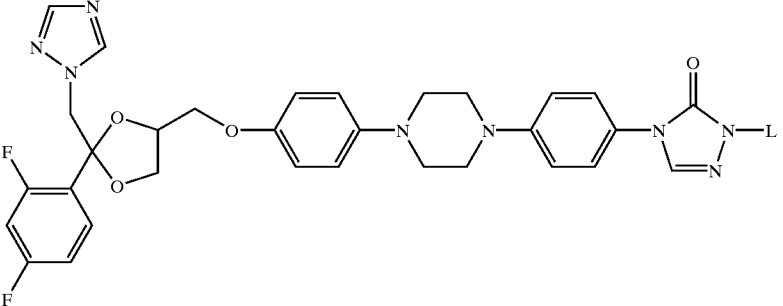 | [2S-[2α,4α[(R*,R*)(R*)]]]; $[α]_{20}^{D}$ = −47.62 at concentration of 26.04 mg/5 ml DMF; mp. 85.5° C. |

C. PHYSICOCHEMICAL EXAMPLE

Example C1

Water Solubility

An excess of compound was added to water buffered with 0.1 M citric acid and 0.2 M $Na_2HPO_4$ in a ratio of 61.5/38.5 (pH=4). The mixture was shaken during 1 day at room temperature. The precipitate was filtered off. The concentration of the compound was measured via UV spectroscopy and is shown in Table 2.

TABLE 2

| Comp.No. | pH | solubility in mg/ml |
|---|---|---|
| 1 | 4.05 | >10 |
| 3 | 3.65 | >7.09 |
| 4 | 4.4 | >9.8 |
| 5 | 4.05 | >12 |

D. PHARMACOLOGICAL EXAMPLE

Example D1

Determination of Fungal Susceptibility.

A panel of Candida isolates plus single isolates of the dermatophytes *Microsporum canis, Trichophyton rubrum and Trichophyton mentagrophytes; Aspergillus fumigatus*, and *Cryptococcus neoformans* were used to evaluate the activity of the test compounds in vitro. Inocula were prepared as broth cultures (yeasts) or as suspensions of fungal material made from agar slope cultures (moulds). The test compounds were pipetted from dimethylsulfoxide stock solution into water to provide a series of 10-fold dilutions. The fungal inocula were suspended in the growth medium CYG (F. C. Odds, Journal of Clinical Microbiology, 29, 2735–2740, 1991) at approximately 50,000 colony-forming units (CFU) per ml and added to the aqueous test drugs. The cultures were set up in the 96 wells of plastic microdilution plates and they were incubated for 2 days at 37° C. (Candida spp.) or for 5 days at 30° C. (other fungi). Growth in the microcultures was measured by their optical density (OD) measured at a wavelength of 405 nm. The OD for cultures with test compounds was calculated as a percentage of the OD for control cultures, i.e. the OD for cultures without test compounds. Inhibition of growth to 35% of control or less was recorded as significant inhibition.

Minimal inhibitory concentration (MIC; in $10^{-6}$ M) of some of the compounds of formula (I) for *Candida glabrata, Candida krusei, Candida parapsilosis, Candida albicans, Candida kefyr, Candida tropicalis, Microsporum canis, Trichophyton rubrum, Trichophyton mentagrophytes, Cryptococcus neoformans* and *Aspergillus fumigatus* are listed in table 3.

TABLE 3

| | MIC values in $10^{-6}$ M | | |
|---|---|---|---|
| Infection | Comp. 1 | Comp. 3 | Comp. 5 |
| *Candida albicans* | 0.1 | <0.01 | <0.1 |
| *Candida glabrata* | 10 | 1 | 10 |
| *Candida krusei* | 10 | 1 | 10 |
| *Candida parapsilosis* | 0.1 | <0.01 | <0.1 |
| *Candida kefyr* | 0.1 | <0.01 | <0.1 |
| *Candida tropicalis* | 0.1 | 0.1 | 1 |
| *Microsporum canis* | 10 | 1 | <0.1 |
| *Trichophyton rubrum* | 1 | 0.1 | 10 |
| *Trichophyton mentagrophytes* | 10 | 1 | 10 |
| *Cryptococcus neoformans* | 1 | 0.1 | 1 |
| *Aspergillus fumigatus* | 10 | 1 | 1 |

E. COMPOSITION EXAMPLE

"Active ingredient" (A.I.) as used throughout these examples relates to a compound of formula (I), a N-oxide, a salt, a quaternary amine or a stereochemically isomeric form thereof.

Example E1

Injectable Solution.

1.8 Grams methyl 4-hydroxybenzoate and 0.2 grams sodium hydroxide were dissolved in about 0.5 l of boiling water for injection. After cooling to about 50° C. there were added while stirring 0.05 grams propylene glycol and 4 grams of the active ingredient. The solution was cooled to room temperature and supplemented with water for injection q.s. ad 1 l, giving a solution comprising 4 mg/ml of active ingredient. The solution was sterilized by filtration and tilled in sterile containers.

Example E2

Transungual Composition 0.144 g $KH_2PO_4$, 9 g NaCl, 0.528 g $Na_2HPO_4.2H_2O$ was added to 800 ml $H_2O$ and the mixture was stirred. The pH was adjusted to 7.4 with NaOH and 500 mg $NaN_3$ was added. Ethanol (42 v/v %) was added and the pH was adjusted to 2.3 with HCl. 15 mg active ingredient was added to 2.25 ml PBS (Phosphate Buffer Saline)/Ethanol (42%; pH 2.3) and the mixture was stirred and treated with ultrasound. 0.25 ml PBS/Ethanol (42%; pH2.3) was added and the mixture was further stirred and treated with ultrasound until all active ingredient was dissolved, yielding the desired transungual composition.

Example E3

Oral Drops

500 Grams of the A.I. was dissolved in 0.5 l of a sodium hydroxide solution and 1.5 l of the polyethylene glycol at 60–80° C. After cooling to 30–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example E4

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example E5

Film-coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10,000 tablets, each containing 10 mg of the active ingredient.

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example E6

2% Cream

Stearyl alcohol (75 mg), cetyl alcohol (20 mg), sorbitan monostearate (20 mg) and isopropyl myristate (10 mg) are introduced in a doublewall jacketed vessel and heated until the mixture has completely molten. This mixture is added to a seperately prepared mixture of purified water, propylene glycol (200 mg) and polysorbate 60 (15 mg) having a temperature of 70 to 75° C. while using a homogenizer for liquids. The resulting mixture is allowed to cool to below 25° C. while continuously mixing. A solution of A.I.(20 mg), polysorbate 80 (1 mg) and purified water q.s. ad 1 g and a solution of sodium sulfite anhydrous (2 mg) in purified water are next added to the emulsion while continuously mixing. The cream is homogenized and filled into suitable tubes.

Example E7

2% Cream

A mixture of A.I. (2 g), phosphatidyl choline (20 g), cholesterol (5 g) and ethyl alcohol (10 g) is stirred and heated at 55–60° C. until complete solution and is added to a solution of methyl paraben(0.2 g), propyl paraben (0.02 g), disodium edetate (0.15 g) and sodium chloride (0.3 g) in purified water (ad 100 g) while homogenizing. Hydroxypropylmethylcellulose (1.5 g) in purified water is added and the mixing is continued until swelling is complete.

What is claimed is:

1. A compound of formula

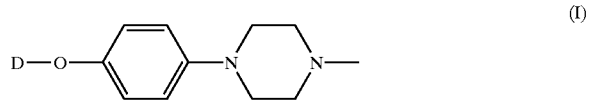

(I)

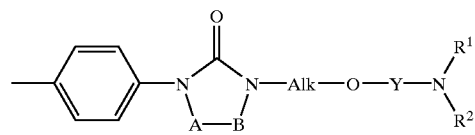

a N-oxide form, a salt, a quaternary amine or stereochemically isomeric form thereof, wherein D represents a radical of formula

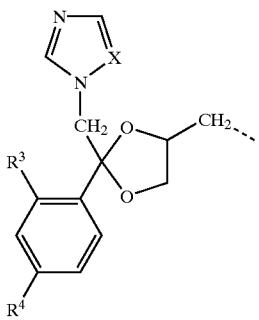
(D₁)

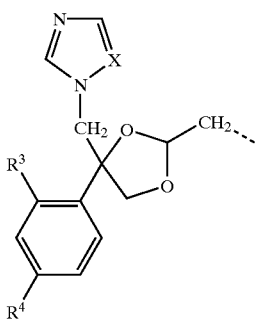
(D₂)

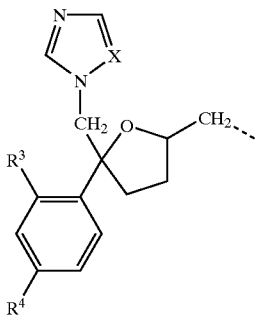
(D₃)

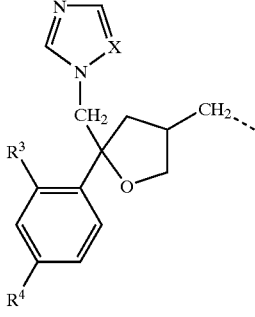
(D₄)

wherein the dotted line represents the bond attaching D to the remainder of the compound of formula (I);
X is N or CH;
R³ is hydrogen or halo;
R⁴ is halo;
—A—B— represents a bivalent radical of formula:

—N=CH—     (i),
—CH=N—     (ii),
—CH=CH—    (iii),
—CH₂—CH₂   (iv), wherein one hydrogen atom in the radicals (i) and (ii) may be replaced by a $C_{1-4}$alkyl radical and one or more hydrogen atoms in radicals (iii) and (iv) may be replaced by a $C_{1-4}$alkyl radical;

Alk represents $C_{1-6}$alkanediyl;

Y represents $C_{1-6}$alkanediyl optionally substituted with one or two substituents selected from halo, hydroxy, mercapto, $C_{1-4}$alkyloxy, $C_{1-4}$alkylthio, aryloxy, arylthio, aryl$C_{1-4}$alkyloxy, aryl$C_{1-4}$alkylthio, cyano, amino, mono- or di($C_{1-4}$alkyl)amino, mono- or di(aryl)amino, mono- or di(aryl$C_{1-4}$alkyl)amino, $C_{1-4}$alkyloxycarbonylamino, benzyloxycarbonylamino, aminocarbonyl, carboxyl, $C_{1-4}$alkyloxycarbonyl, guanidinyl, and aryl;

$R^1$ represents hydrogen, $C_{1-6}$alkyl or aryl$C_{1-6}$alkyl;

$R^2$ represents hydrogen, $C_{1-6}$alkyl or aryl$C_{1-6}$alkyl; or $R^1$ and $R^2$ may be taken together to form a heterocyclic radical selected from morpholinyl, pyrrolidinyl, piperidinyl, homopiperidinyl, piperazinyl or phthalimid-1-yl; said heterocyclic radical may optionally be substituted with $C_{1-4}$alkyl, aryl, aryl$C_{1-4}$alkyl, hydroxy$C_{1-4}$alkyl, amino, mono- or di($C_{1-4}$alkyl)amino, amino$C_{1-4}$alkyl, mono- or di($C_{1-4}$alkyl)amino$C_{1-4}$alkyl, carboxyl, aminocarbonyl, $C_{1-4}$alkyloxycarbonyl, $C_{1-4}$alkyloxycarbonylamino or mono- or di($C_{1-4}$alkyl)aminocarbonyl;

aryl represents phenyl, naphthalenyl, 1,2,3,4-tetrahydro-naphthalenyl, indenyl or indanyl; each of said aryl groups may optionally be substituted with one or more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy$C_{1-4}$alkyl, amino$C_{1-4}$alkyl, mono- or di($C_{1-4}$alkyl)amino$C_{1-4}$alkyl.

2. A compound according to claim 1 wherein —Alk— is a bivalent radical of formula

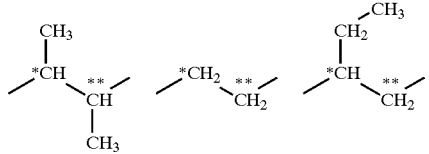

wherein the carbon atom marked with one asterisk is attached to the nitrogen atom and the carbon atom marked with two asterisks is attached to the oxygen atom.

3. A compound according to claim 1 wherein D is a radical of formula $D_1$ or $D_2$.

4. A compound according to claim 1 wherein Y is $C_{1-6}$alkanediyl optionally substituted with aryl.

5. A compound according to claim 1 wherein —A—B— is a radical of formula (ii).

6. A compound according to claim 1 which is stereoisomerically pure.

7. A method for treating fungal infections in a patient, comprising administering an effective amount of a compound according to claim 1 to said patient.

8. A pharmaceutical composition comprising a pharmaceutically acceptable carrier, and as active ingredient a therapeutically effective amount of a compound as claimed in claim 1.

9. A process of preparing a composition as claimed in claim 8 comprising combining a pharmaceutically acceptable carrier with a therapeutically effective amount of said compound.

10. A process of preparing a compound according to claim 1, comprising a) reacting an intermediate of formula (II) with an intermediate of formula (III) in a reaction-inert solvent and in the presence of a suitable base

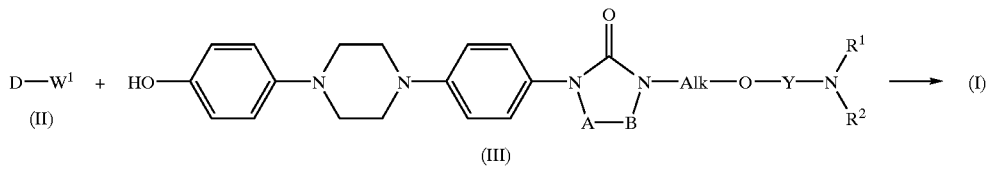

wherein $W^1$ is a suitable leaving group;

b) N-alkylating an intermediate of formula (IV) with an intermediate of formula (V) in a reaction-inert solvent in the presence of a base

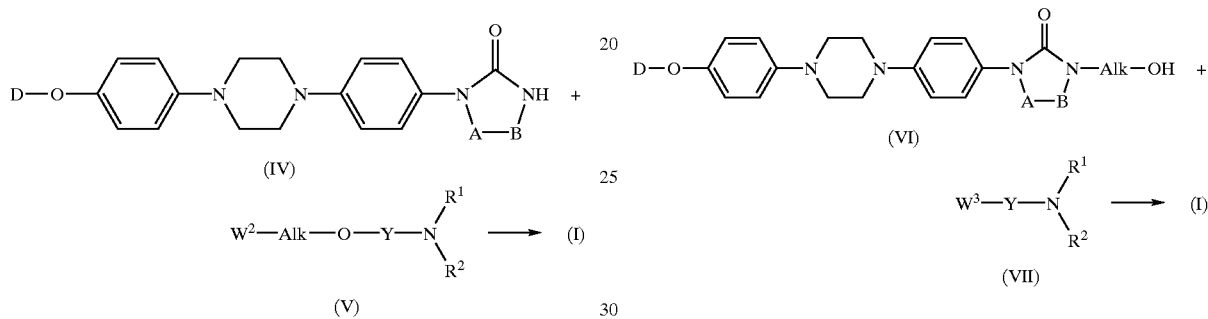

wherein $W^2$ is a suitable leaving group; and in case one or more of R1 and $R^2$ is hydrogen, the primary or secondary amine group in intermediate (V) is protected with a suitable protective group P and after the N-alkylation reaction, the protected primary or secondary amine group is deprotected to provide compounds of formula (I);

c) reacting an intermediate of formula (VI) with an intermediate of formula (VII), optionally in the presence of a suitable base and optionally in a reaction-inert solvent

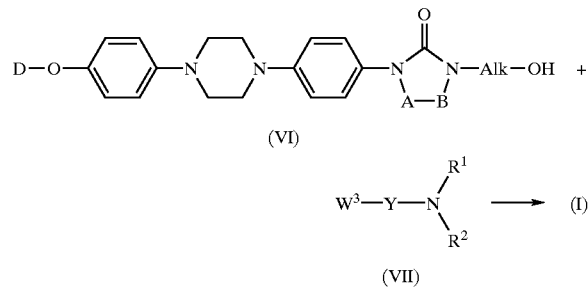

wherein $W^3$ is a suitable leaving group; and in case one or more of $R^1$ and $R^2$ is hydrogen, the primary or secondary amine group in intermediate (VII) is protected with a suitable protective group P and after the O-alkylation reaction, the protected primary or secondary amine group is deprotected to provide compounds of formula (I).

* * * * *

UNITED STATES PATENT AND TRADEMARK OFFICE
CERTIFICATE OF CORRECTION

PATENT NO.   : 6,583,136 B1
DATED        : June 24, 2003
INVENTOR(S)  : Meerpoel et al.

It is certified that error appears in the above-identified patent and that said Letters Patent is hereby corrected as shown below:

<u>Column 6,</u>
Line 17, please delete "trains" and insert therefore -- trans --;
Line 23, please delete "(D2)" and insert therefore -- ($D_2$) --;

<u>Column 8,</u>
Line 9, please delete "R" and insert therefore -- $R^2$ --;
Line 34, please delete "W3" and insert therefore -- $W^3$ --;

<u>Column 26,</u>
Line 34, please delete "R1" and insert therefore -- $R^1$ --;

Signed and Sealed this

Twenty-fourth Day of February, 2004

JON W. DUDAS
*Acting Director of the United States Patent and Trademark Office*